United States Patent [19]

Nascimento et al.

[11] Patent Number: 5,158,935
[45] Date of Patent: Oct. 27, 1992

[54] HUMAN EPIDERMAL GROWTH FACTOR HAVING SUBSTITUTION AT POSITION 11

[75] Inventors: Carlos G. Nascimento, Danville; Angelica Medina-Selby, San Francisco, both of Calif.

[73] Assignee: Chiron Corporation, Emeryville, Calif.

[21] Appl. No.: 351,773

[22] Filed: May 12, 1989

[51] Int. Cl.⁵ .................. A61K 37/36; C07K 13/00
[52] U.S. Cl. .................................. 514/12; 530/399; 530/350
[58] Field of Search .............. 514/21, 925; 530/339, 530/324

[56] References Cited

U.S. PATENT DOCUMENTS

| | | | |
|---|---|---|---|
| 4,621,052 | 11/1986 | Sugimoto | 435/68 |
| 4,628,186 | 7/1985 | Nishimura et al. | 424/99 |
| 4,686,283 | 8/1987 | Nestor, Jr. et al. | 514/15 |
| 4,717,717 | 1/1988 | Finkenaur | 514/21 |
| 4,743,679 | 5/1988 | Cohen et al. | 530/350 |
| 4,948,875 | 4/1976 | Cohen et al. | 530/324 |

FOREIGN PATENT DOCUMENTS 046039 2/1982 European Pat. Off. .

OTHER PUBLICATIONS

Carpenter et al., *Ann. Rev. Biochem.* (1979) 48:193–216.
Gregory et al., *Int. J. Peptide Protein Res.* (1977) 9:107–118.
Urdea et al., *Proc. Natl. Acad. Sci.* (1983) 80:7461–7465.
Oka et al., *Proc. Natl. Acad. Sci.* (1985) 82:7212–7216.
George-Nascimento et al., *Biochem.* (1988) 27:797–802.
Makino et al., *Proc. Natl. Acad. Sci.* (1987) 84:7841–7845.
McFadden et al., *Proc. Natl. Acad. Sci.* (1987) 84:2595–2599.
Murray et al., *J. Bio. Chem.* (1984) 259:10722–10732.
Johnson et al., *J. Bio. Chem.* (1985) 260:10913–10916.
Brake et al., *Proc. Natl. Acad. Sci.* (1984) 81:4642–4646.
Tom Alber, *Annu. Rev. Biochem.* 58 765–98 (1989), "Mutational Effects on Protein Stability".
Tom Alber, et al., *Nature,* 330, 41–46 (1987) "Contributions of Hydrogen Bonds of Thr 157 to The Thermodynamic Stability of phage T₄ Lysozyone".

*Primary Examiner*—F. T. Moezie
*Attorney, Agent, or Firm*—Morrison & Foerster

[57] ABSTRACT

We have now found that one may improve the storage life of EGF without diminishing its biological activity by replacing the Asp at position 11 with a different amino acid, preferably Glu, Asn, Gln, Ala, or Lys, more preferably Glu, or Asn, and most preferably Glu. Other modifications may additionally be made, most preferably by substituting Met$_{21}$ (which we have found is susceptible to oxidation) with Ile or a similar amino acid.

2 Claims, 2 Drawing Sheets

HUMAN EPIDERMAL GROWTH FACTOR HAVING SUBSTITUTION AT POSITION 11

DESCRIPTION

1. Technical Field

This invention relates to the molecular biology of cellular growth factors and recombinant DNA technology. More specifically, this invention relates to epidermal growth factor (EGF) modified to increase its chemical stability, and the therapeutic uses of modified EGF of the invention.

2. Background of the Invention

Epidermal growth factor (EGF) is a 53-amino acid protein synthesized in the duodenum and salivary glands of normal humans, and normally excreted in the urine. For its effect in reducing gastric acid secretion, and its first isolation source, it was formerly termed urogastrone. After it was sequenced, it was recognized that urogastrone was homologous to murine EGF, and that urogastrone additionally stimulated the proliferation of certain cell types, prompting a change in nomenclature to EGF. The biological and chemical properties of hEGF and mEGF are reviewed in G. Carpenter et al, *Ann Rev Biochem* (1979) 48:193–216.

The amino acid sequence of human EGF is:
Asn Ser Asp Ser Glu Cys Pro Leu Ser His
Asp Gly Tyr Cys Leu His Asp Gly Val Cys
Met Tyr Ile Glu Ala Leu Asp Lys Tyr Ala
Cys Asn Cys Val Val Gly Tyr Ile Gly Glu
Arg Cys Gln Tyr Arg Asp Leu Lys Trp Trp
Glu Leu Arg This sequence was published by H. Gregory et al, *Int J Peptide Protein Res* (1977) 9:107–18, who isolated the protein as urogastrone from human urine (1 mg/1000 L), and disclosed its sequence homology with mEGF. Murine EGF has the sequence (differences from hEGF underlined):

Asn Ser Tyr Pro Gly Cys Pro Ser Ser Tyr
Asp Gly Tyr Cys Leu Asn Gly Gly Val Cys
Met His Ile Glu Ser Leu Asp Ser Tyr Thr
Cys Asn Cys Val Ile Gly Tyr Ser Gly Asp
Arg Cys Gln Thr Arg Asp Leu Arq Trp Trp
Glu Leu Arg, which conserves the disulfide bonds. Gregory also discloses that urogastrone may be maintained in aqueous solution at pHs of 1–11 for at least 20 hours without loss of activity, and that the six C-terminal amino acids may be removed without loss of biological activity.

Preparation of an hEGF gene is described in EPO 046,039, and cloning and expression of EGF is disclosed in commonly-owned copending U.S. patent application Ser. No. 004,212, filed Jan. 5, 1987, a continuation of Ser. No. 457,412, filed Jan. 12, 1983, now abandoned. U.S. Ser. No. 004,212 is incorporated herein by reference in full. Other disclosures of EGF preparation are M. S. Urdea et al, *Proc Nat Acad Sci USA*, (1983) 80:7461–65 (chemical synthesis of gene and expression in yeast), T. Oka et al, *Proc Nat Acad Sci USA*, (1985) 82:7212–16 (fusion protein in *E. coli*); Cohen et al, U.S. Pat. No. 4,743,679 (recombinant fusion protein); Sugimoto, U.S. Pat. No. 4,621,052 (human hybridoma cell culture); Nishimura et al, U.S. Pat. No. 4,528,186 (adsorption from urine); and Cohen et al, U.S. Pat. No. 3,948,875 (purification from murine submaxillary glands). Pharmaceutical compositions containing EGF are disclosed in Finkenaur, U.S. Pat. No. 4,717,717 (stabilized against degradation by moisture with water-soluble cellulose derivatives); U.S. Pat. No. 4,703,108 (cross-linked collagen sponge); and Camble et al, U.S. Pat. No. 3,917,824 (lyophilized solid or dextrose solution)

C. George-Nascimento et al, *Biochem* (1988) 27:797–802 reported the isolation from recombinant yeast culture of four distinct forms of EGF, termed A, B, C, and D, each of which exhibit full EGF activity. EGF-D represents the 52-amino acid sequence obtained by removing the C-terminal arg, while EGF-B corresponds to EGF-D wherein the C-terminal arg-leu has been removed. EGF-C appears to be EGF-D in which $Met_{21}$ has been oxidized, while EGF-A appears to be EGF-B with $Met_{21}$ oxidized. EGF-D is reported to be stable when stored as a lyophilized powder.

The physical structure of a recombinantly-produced hEGF has been partially elucidated using COSY and NOESY by K. Makino et al, *Proc Nat Acad Sci USA*, 84:7841–45 (1987). Makino disclosed that amino acids 19–32 form an antiparallel beta-pleated sheet, placing $His_{10}$ in close proximity to $Tyr_{22}$ and $Tyr_{29}$. Makino also suggested that amino acids 45–53 may form an alpha helix which crosses the surface of the beta-pleated sheet, creating a hydrophobic pocket comprising $His_{10}$, $Tyr_{22}$, $Tyr_{29}$, $Trp_{49}$, and $Trp_{50}$. Removal of amino acids 49–53 altered the nmr chemical shift and $pK_a$ of the ring protons on $His_{10}$, $His_{19}$, $Tyr_{22}$, and $Tyr_{29}$, and drastically reduced the activity, suggesting that these amino acids may participate in the EGF binding site.

Nestor et al, U.S. Pat. No. 4,686,283 disclosed the preparation of polypeptides and polypeptide analogs homologous to amino acids 34–43 of EGF and TGF-alpha, which are useful as EGF antagonists and for preparing anti-EGF antibodies.

DISCLOSURE OF THE INVENTION

We have now discovered that EGF under conventional conditions of storage is subject to an intramolecular chemical reaction which results in a detrimental conformational change in the protein. More specifically, we have determined that $Asp_{11}$ forms a succinimidyl ring by an intramolecular amidation of the side chain carboxyl group by the adjacent (Gly12) peptidyl nitrogen. This succinimidyl ring may then hydrolyze, either regenerating the original Asp residue, or forming an iso-asp residue which effects a homologation of the peptide backbone. Spontaneous degradation by conversion of Asp or Asn to iso-asp has been proposed in the art for proteins other than EGF: see, e.g., P. N. McFadden et al, *Proc Nat Acad Sci USA*, (1987) 84:2595–99 (tetragastrin); E. D. Murray et al, *J Biol Chem* (1984) 259:10722–32 (ACTH hexapeptide derivative); B. A. Johnson et al, *J Biol Chem* (1985) 260:10913–16 (calmodulin). Proteins containing the sequence Asp-Gly are believed particularly susceptible. However, there is no suggestion in the art that human EGF would be susceptible to Asp isomerization, or that such isomerization would adversely affect EGF,s biological activity.

We have now found that one may improve the storage life of EGF without diminishing its biological activity by replacing the Asp at position 11 with a different amino acid, preferably Glu, Asn, Gln, Ala, or Lys, more preferably Glu, or Asn, and most preferably Glu. Other modifications may additionally be made, most preferably by substituting $Met_{21}$ (which we have found is susceptible to oxidation) with Ile or a similar amino acid.

BRIEF DESCRIPTION OF THE DRAWINGS

FIG. 1 depicts RP-HPLC chromatograms illustrating the stability of rhEGF-Glu$_{11}$ under low pH and high temperature.

FIG. 2 depicts RP-HPLC chromatograms illustrating the degradation of rhEGF under low pH and high temperature.

MODES OF CARRYING OUT THE INVENTION

A. Definitions

Figure 1A:
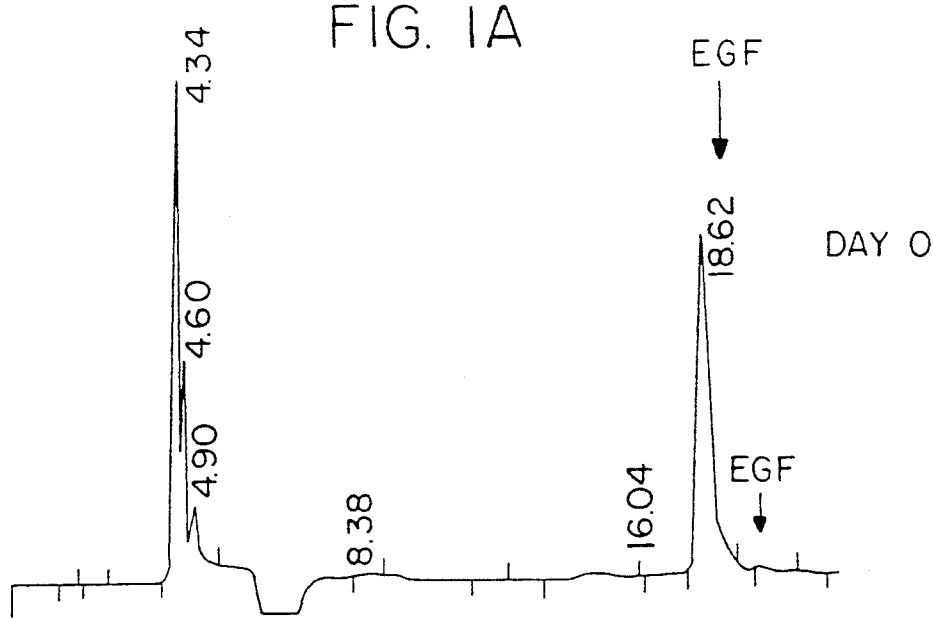
FIG. 1A shows the chromatogram obtained on day 0.
Figure 1B:
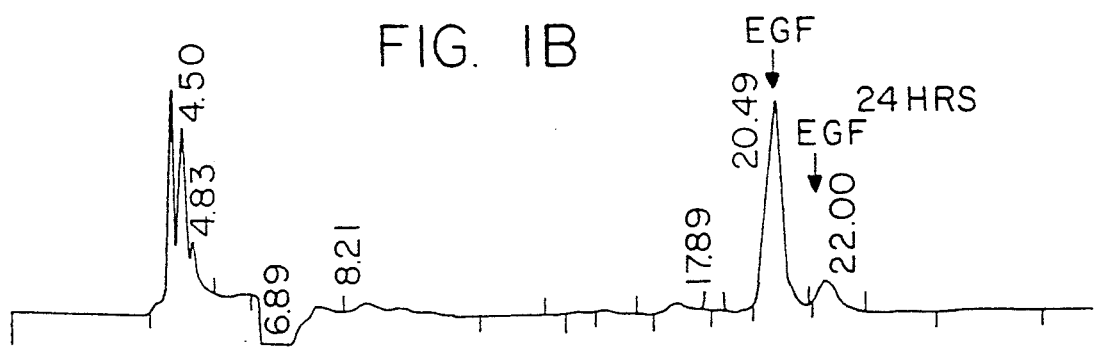
FIGS. 1B–D show the chromatograms obtained on days 1, 7 and 15.
Figure 1C:
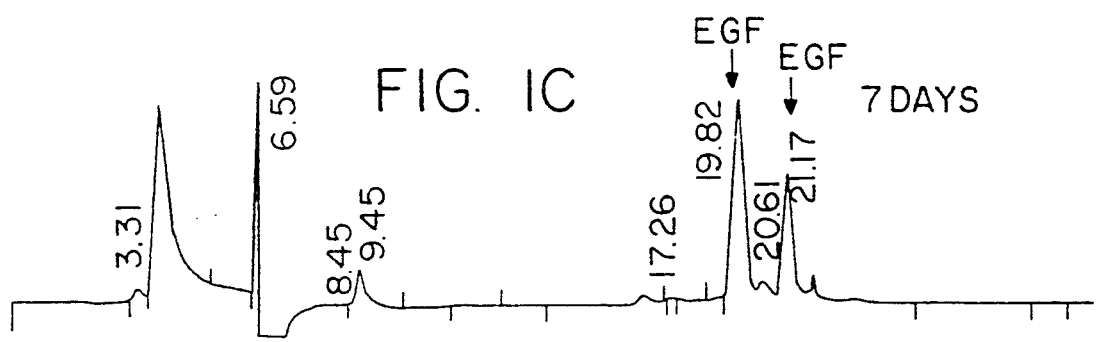
Figure 1D:
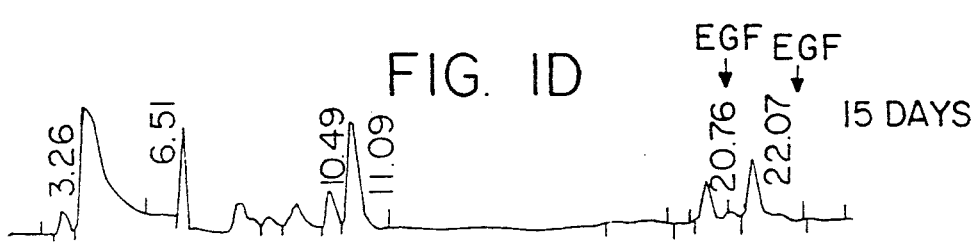
Figure 2A:
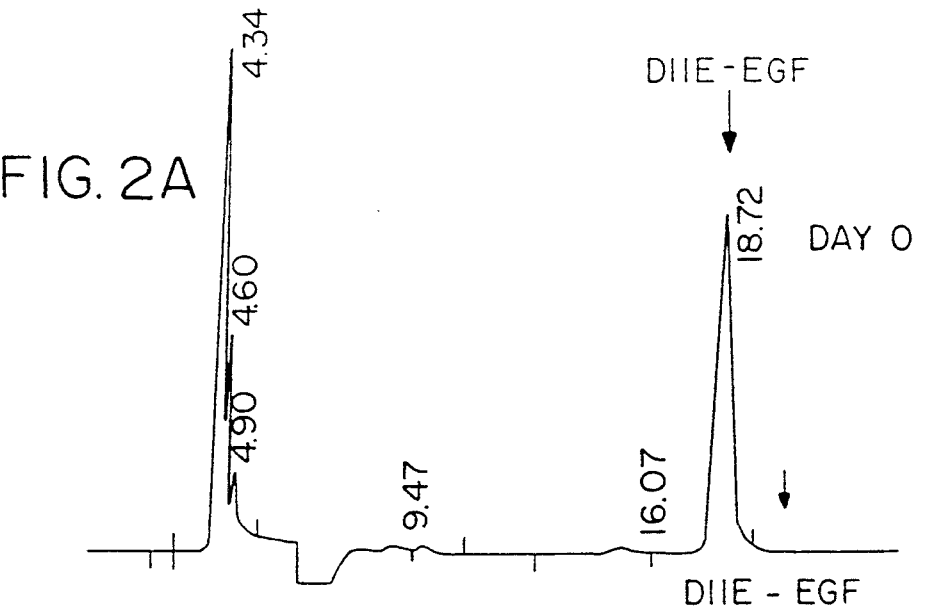
FIG. 2A shows the chromatogram obtained on day 0.
Figure 2B:
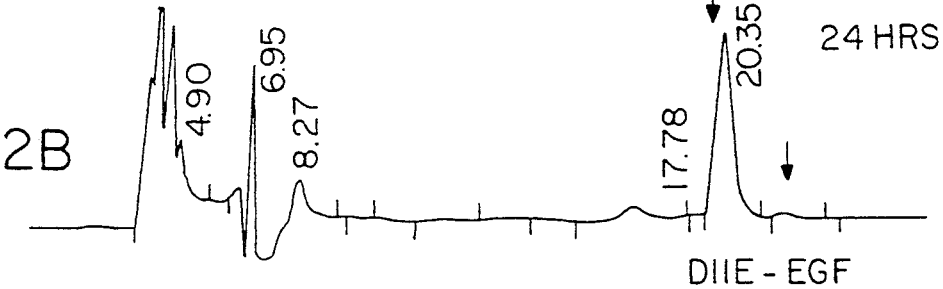
FIGS. 2B–D show the chromatograms obtained on days 1, 7 and 15.
Figure 2C:
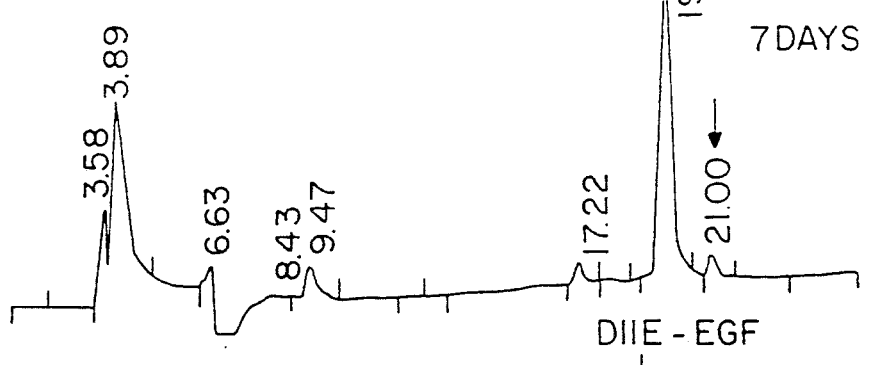
Figure 2D:
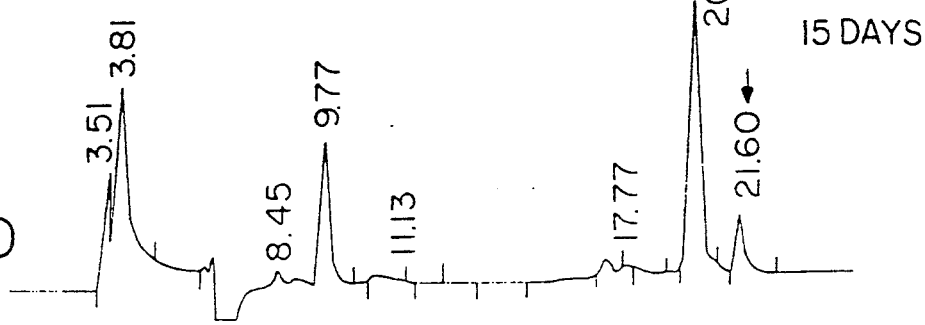

The term "EGF" as used herein refers to a polypeptide having substantially the same sequence and activity as purified native epidermal growth factor. The term "hEGF" denotes the EGF protein having the substantially the same sequence and characteristics as epidermal growth factor obtained from humans, while "rhEGF" specifies that the hEGF is produced by recombinant methods. Similarly, "mEGF" denotes EGF of murine origin, and "rmEGF" denotes EGF having the murine sequence prepared by recombinant means. "EGF" includes proteins varying from the native sequence, e.g., by substitution of one or more amino acids with other amino acids, so long as the EGF biological activity is substantially preserved. EGF biological activity is preferably measured by a receptor binding assay. "Substantially similar" sequences are those which preferably have at least 65 number% homology with the native sequence, more preferably about 85 number%, still more preferably about 90 number%, and most preferred about 95 number%. Thus, for example, a human EGF protein in which the methionine (Met) at position 21 is replaced with isoleucine (Ile) falls within the scope of "EGF." Such a protein is denoted hEGF-Ile generally, and is denoted rhEGF-Ile$_{21}$ if prepared recombinantly (chemically synthesized hEGF is included in the term "hEGF"). Similarly, hEGF having the Asp at position 11 replaced with Glu is denoted hEGF-Glu$_{11}$. Some EGF proteins truncated near the carboxy terminal retain their biological activity, and are denoted with a subscript indicating the last peptide residue retained. Thus, EGF lacking the last 2 of its normal 53 peptides is indicated EGF$_{51}$. Proteins having an amino acid deletion, for example wherein trp$_{49}$ is absent, are denoted with the term "del" and a subscript indicating the position, without altering the numbering of the remaining amino acids. Thus, if trp49 were deleted, the resulting protein would be indicated EGF-del$_{49}$. Insertions, increasing the chain length, are indicated as substitutions substituting 2 or more amino acids for one, e.g., rhEGF-Leu/Gly$_{15}$ indicates insertion of gly after the natural Leu15. Finally, an EGF of the invention where Asp$_{11}$ has been replaced by another amino acid, with or without other modifications, is denoted generically by EGF-xxx$_{11}$.

The term "amino acid" as used herein refers generally to a molecule of the formula NH$_2$-CHR—COOH, wherein R is a side chain or residue which may or may not occur naturally. The terms "natural amino acid" and "naturally-occurring amino acid" refer to those 20 amino acids which are the normal constituents of proteins, e.g., Ala, Asp, Cys, Glu, Phe, Gly, His, Ile, Lys, Leu, Met, Asn, Pro, Gln, Arg, Ser, Thr, Val, Trp, Tyr. Other (non-natural) amino acids which may be used include homoserine, phenylglycine, taurine, iodotyrosine, and the like. Preferably, the side chain (R) of an amino acid will contain 1–12 carbon atoms, 0–4 nitrogen atoms, 0–2 sulfurs, 0–4 oxygens, and 0–4 halogen atoms.

A "condition treatable with EGF" is any disorder or wound having symptoms which may be ameliorated using EGF. For example, EGF is known to reduce secretion and oversecretion of gastric acid. Accordingly, EGF-xxx$_{11}$ may be used to treat gastric and duodenal ulcers, as well as gastric hyperacidity. EGF is also known to improve healing of epithelial wounds, including wounds to the eye, e.g., caused by trauma (including surgery), infection, and the like. Accordingly, EGF-xxx$_{11}$ may be administered to epithelial wounds to improve wound healing. EGF-xxx$_{11}$ is particularly useful in corneal storage media, for preserving the epithelial and endothelial cell layers on corneal explants stored for subsequent transplantation. As corneal explants may be stored for period of up to about three months, it is extremely useful to use a form of EGF which is not chemically degraded over that time period.

B. General Method

The proteins of the invention may be prepared either by traditional chemical means, or by recombinant means. The 53 amino acid length of EGF is within the practical limits for use of commercially available peptide synthesizers, which comprises the most convenient method for preparing those EGF-xxx$_{11}$ derivatives of the invention which contain non-natural amino acids. The use of such commercial machines is well-known in the art, and needs no further description.

However, recombinant methods of production are currently more economical, and more amenable to commercial manufacture. Further, recombinant expression in eukaryotic cells (e.g., yeast) generally provides EGF which is correctly folded and disulfide-linked.

Expression

The proteins of the invention may be expressed in either prokaryotic or eukaryotic systems, or in in vitro expression systems. Prokaryotes are most frequently represented by various strains of *E. coli*. However, other microbial strains may also be used, such as bacilli (for example *Bacillus subtilis*), various species of *Pseudomonas*, and other bacterial strains. In such prokaryotic systems, plasmid vectors which contain replication sites and control sequences derived from a species compatible with the host are use. For example, *E. coli* is typically transformed using derivatives of pBR322, a plasmid derived from an *E. coli* species by Bolivar et al, *Gene* (1977) 2:95. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al, *Nature* (1977) 198:1056) and the tryptophan (trp) promoter system (Goeddel et al, *Nucleic Acids Res* (1980)8:4057) and the lambda-derived P$_L$ promoter and N-gene ribosome binding site (Shimatake et al, *Nature* (1981) 292:128). However, any availabl promoter system compatible with prokaryotes can be used.

The expression systems useful in eukaryotic systems of the invention comprise promoters derived from appropriate eukaryotic genes. A class of promoters useful in yeast, for example, include promoters for synthesis of glycolytic enzymes, including those for 3-phosphoglycerate kinase (Hitzeman et al, *J Biol Chem* (1980) 255:2073), and especially glyceraldehyde 3-phosphate dehydrogenase (GAPDH) (M.S. Urdea et al, *Proc Nat Acad Sci USA* (1983) 80:7461–65). Other promoters include those from the enolase gene (M. J. Holland et al, *J Biol Chem* (1981) 256:1385) or the Leu2 gene obtained from YEp13 (J. Broach et al, *Gene* (1978) 8:121).

Suitable mammalian promoters include the early and late promoters from SV40 (Fiers et al, *Nature* (1978) 273:113) or other viral promoters such as those derived from polyoma, adenovirus II, bovine papilloma virus, or avian sarcoma viruses. Suitable viral and mammalian enhancers are cited above. In the event plant cells are used as an expression system, the nopaline synthesis promoter is appropriate (A. Depicker et al, *J Mol Appl Gen* (1982) 1:561). Expression in insect cell culture may conveniently be achieved using a baculovirus vector.

One may express rEGF-xxx$_{11}$ in vitro, and incorporate "non-natural" amino acids using the technique disclosed by C. J. Noren et al, Science (1989) 244:182–88. Briefly, an in vitro expression vector is prepared (e.g., and SP6 plasmid), and the codon position corresponding to the non-natural amino acid site is altered to a nonsense codon (particularly TAG), e.g., using oligonucleotide-directed mutagenesis. A corresponding tRNA is prepared and acylated in vitro with the desired non-natural amino acid (e.g., 4-fluorophenylalanine, phenylglycine, and the like). Expression of the altered vector in a cell-free system in the presence of the acylated tRNA provides the polypeptide incorporating the non-natural amino acid.

Transformation

Depending on the host cell used, transformation is done using standard techniques appropriate to such cells. The calcium treatment employing calcium chloride, as described by S. N. Cohen, *Proc Nat Acad Sci USA* (1972) 69:2110, or the RbCl method described in Maniatis et al, *Molecular Cloning: A Laboratory Manual* (1982) Cold Spring Harbor Press, p. 254, is used for prokaryotes or other cells which contain substantial cell wall barriers. Infection with *Agrobacterium tumefaciens* (C. H. Shaw et al, Gene (1983) 23:315) is used for certain plant cells. For mammalian cells without cell walls, the calcium phosphate precipitation method of Graham and van der Eb, *Virology* (1978) 52:546 is preferred. Alternatively, one may use a liposomal formulation for transfection. A synthetic lipid useful for polynucleotide transfection is N-[1-(2,3-dioleyloxy)propyl]-N,N,N-trimethylammonium chloride, which is commercially available under the name Lipofectin ™ (available from BRL, Gaithersburg, Md.), and is described by P. L. Felgner et al, *Proc Nat Acad Sci USA* (1987) 84:7413. Transformations into yeast are carried out according to the method of P. Van Solingen et al, *J Bacter* (1977) 130:946 and C. L. Hsiao et al, *Proc Nat Acad Sci USA* (1979) 76:3829.

Probing cDNA or Genomic Libraries cDNA or genomic libraries are screened using the colony hybridization procedure. Each microtiter plate is replicated onto duplicate nitrocellulose filter papers (S & S type BA-85) and colonies are allowed to grow at 37° C. for 14–16 hr on L agar containing 50 ug/mL Amp. The colonies are lysed and DNA fixed to the filter by sequential treatment for 5 min with 500 mM NaOH, 1.5 M NaCl, and are washed twice for 5 min each time with 5×standard saline citrate (SSC). Filters are air dried and baked at 80° C. for 2 hr. The duplicate filters are prehybridized at 42° C. for 6–8 hr with 10 mL per filter of DNA hybridization buffer (5X SSC, pH 7.0, 5× Denhardt's solution (polyvinylpyrrolidone, plus Ficoll and bovine serum albumin; 1×0.02% of each), 50 mM sodium phosphate buffer at pH 7.0, 0.2% SDS, 20 ug/mL poly-U, and 50 ug/mL denatured salmon sperm DNA).

The samples are hybridized with kinased probe under conditions which depend on the stringency desired. Typical moderately stringent conditions employ a temperature of 42° C. for 24–36 hr with 1–5 mL/filter of DNA hybridization buffer containing probe. For higher stringencies, high temperatures and shorter times are employed. The filters are washed four times for 30 min each time at 37° C. with 2× SSC, 0.2% SDS and 50 mM sodium phosphate buffer at pH 7, then washed twice with 2× SSC and 0.2% SDS, air dried, and are autoradiographed at −70° C. for 2 to 3 days.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored and religated in the form desired.

Site specific DNA cleavage is performed by treatment with a suitable restriction enzyme (or enzymes) under conditions which are generally understood in the art, generally following the manufacturer's directions. See, e.g., New England Biolabs, Product Catalog. In general, about 1 ug of plasmid or DNA sequence is cleaved by one unit of enzyme in about 20 uL of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by diethyl ether extraction, and the nucleic acid recovered from aqueous fractions by ethanol precipitation followed by separation over a Sephadex ® G-50 spin column. If desired, size separation of the cleaved fragments may be performed by polyacrylamide gel or agarose gel electrophoresis using standard techniques. A general description of size separations is found in *Meth Enzymol* (1980) 65:499–560.

Restriction cleaved fragments may be blunt ended by treating with the large fragment of *E. coli* DNA polymerase I (Klenow) in the presence of the four deoxyribonucleotide triphosphates (dNTPs) using incubation times of about 15 to 25 min at 20° to 25° C. in 50 mM Tris, pH 7.6, 50 mM NaCl, 6 mM MgCl$_2$, 6 mM DTT and 5–10 uM dNTPs. The Klenow fragment fills in at 5' sticky ends but chews back protruding 3' single strands, even though the four dNTPs are present. If desired, selective repair can be performed by supplying only 1–3 of the dNTPs, within the limitations dictated by the nature of the sticky ends. After treatment with Klenow fragment, the mixture is extracted with phenol/chloroform and ethanol precipitated followed by running over a Sephadex ® G-50 spin column. Treatment under appropriate conditions with S1 nuclease results in hydrolysis of any single-stranded portion.

Synthetic oligonucleotides are prepared by the triester method of Matteucci et al, *J Am Chem Soc* (1981) 103:3185, or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM DTT, 1-2 mM ATP, 1.7 pmoles 32P-ATP (2.9 mCi/mmole), 0.1 mM spermidine, and 0.1 mM EDTA.

Ligations are performed in 15-30 uL volumes under the following standard conditions and temperatures: 20 mM Tris-HCl, pH 7.5, 10 mM $MgCl_2$, 10 mM DTT, 33 ug/mL BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 ug/mL total DNA concentrations (5-100 nM total end concentration). Intermolecular blunt end ligations (usually employing a 10-30 fold molar excess of linkers) are performed at 1 uM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{2+}$ using about 1 unit of BAP per ug of vector at 60° C. for about 1 hr. In order to recover the nucleic acid fragments, the preparation is extracted with phenol/chloroform and ethanol precipitated and desalted by application to a Sephadex ® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis may be used. This is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having the mutated form as a single strand; 50% will have the original sequence. The resulting plaques are hybridized with kinased synthetic primer under allele-specific conditions. In general, one may vary the temperature, ionic strength, and concentration of chaotropic agent(s) in the hybridization solution to obtain conditions under which substantially no probes will hybridize in the absence of an "exact match." For hybridization of probes to bound DNA, the empirical formula for calculating optimum temperature under standard conditions (0.9 M NaCl) is $$T(°C.) = 4(N_G + N_C) + 2(N_A + N_T) - 5°C.,$$

where $N_G$, $N_C$, $N_A$, and $N_T$ are the numbers of G, C, A, and T bases in the probe (J. Meinkoth et al, *Anal Biochem* (1984) 138:267-84).

Plaques which hybridize with the probe are then picked, cultured, and the DNA recovered.

Verification of Construction

Correct ligations for plasmid construction may be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al, *Proc Nat Acad Sci USA* (1969) 62:1159, optionally following chloramphenicol amplification (D. B. Clewell, *J Bacteriol* (1972) 110:667). The isolated DNA is analyzed by restriction and/or sequenced by the dideoxy method of F. Sanger et al, *Proc Nat Acad Sci USA* (1977) 74:5463 as further described by Messing et al, *Nucleic Acids Res* (1981) 9:309, or by the method of Maxam and Gilbert, *Meth Enzymol* (1980) 65:499.

Administration

EGF-xxx$_{11}$ is preferably administered orally, topically, or by parenteral means, including subcutaneous and intramuscular injection, implantation of sustained release depots, intravenous injection, intranasal administration, and the like. When used to treat trauma, it may be advantageous to apply EGF-xxx$_{11}$ directly to the wound, e.g., during surgery to correct other damage resulting from the trauma. Accordingly, EGF-xxx$_{11}$ may be administered as a pharmaceutical composition comprising EGF-xxx$_{11}$ in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol ®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene ®(Marion), Aquaphor ® (Duke Laboratories), and the like. Other topical formulations include aerosols, bandages, and other wound dressings. Alternatively, one may incorporate or encapsulate EGF-xxx$_{11}$ in a suitable polymer matrix or membrane, thus providing a sustained-release delivery device suitable for implantation near the site to be treated locally. Other devices include indwelling catheters and devices such as the Alzet ® minipump. Ophthalmic preparations may be formulated using commercially available vehicles such as Sorbicare TM (Allergan), Neodecadron ® (Merck, Sharp & Dohme), Lacrilube ®, and the like. Further, one may provide EGF-xxx$_{11}$ in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The amount of EGF-xxx$_{11}$ required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 10-1,000 ng/Kg EGF-xxx$_{11}$ administered i.v. or subcutaneously is effective for inhibiting gastric acid secretion. For treating wounds, EGF-xxx$_{11}$ may be administered locally in a gel or matrix at a concentration of about $10^{-12}$ to $10^{-9}$ M.

C. Examples

The examples presented below are provided as a further guide to the practitioner of ordinary skill in the art, and are not to be construed as limiting the invention in any way.

EXAMPLE 1

(Preparation of EGF-Glu$_{11}$ Expression Vector)

(A) An expression vector encoding EGF-Glu$_{11}$ was prepared as follows:

pGAP/EGF

Plasmid pYalphaEGF-25 was prepared following the procedure disclosed by A. J. Brake et al, *Proc Nat Acad Sci USA* (1984) 81:4642-46. This plasmid contains an hEGF synthetic gene fused to the alpha-factor (aF) leader, under control of the aF promoter and terminator. This expression cassette was inserted into the yeast vector pCl/1 (described in Brake, supra), which contains sequences derived from pBR322 and the yeast 2 micron sequence. The aF promoter and terminator were then replaced with a strong promoter and terminator, derived from yeast glyceraldehyde-3-phosphate dehydrogenase (GAP) disclosed by R. L. Burke et al, U.S.Ser. No. 760,197, incorporated herein by reference in full. The resulting plasmid was named pYGAPalphaEGF-25, now abreviated pGAP/ EGF.

pBR322/Short leader-EGF

Plasmid pGAP/EGF was digested to completion with BamHI and HpaII to provide a 504 bp fragment containing the short GAP promoter and 33 amino acids (aa) from yeast aF. A linker having the following sequence was synthesized:

LysArgAsnSerAspSerGluCysProLeuSerHisAsp-
   GlyTyr-CGG        GTAAAAGAAACTC-
CGAATGTCCATTGACCACGACGGCTAC-
CGA       TTTTCTTTGAGGCTTACAGG-
TAACTCGTGCTGCCGATG-
CysLeuHisAspGlyValCysMetTyrIle
TGTTTGCACGACGGTGTTTGTATG-
TACATCGA
ACAAACGTGCTGCCACAAACATACATG-
TAGCTTCGA

This linker encodes 4aa from aF, and 23aa from EGF. The linker and the 504 bp fragment from pGAP/EGF were ligated in pBR322 digested with BamHI and HindIII to form pBR322/Short leader-EGF. This plasmid was transformed into competent HB101 cells, and positive transformants identified by BamHI and HindIII restriction pattern, confirmed by BglI digestion.

pAB24/Short/D11E

Plasmid pBR322/Short leader-EGF was digested with BamHI and BglI to provide a 547 bp fragment comprising the short GAP promoter, 81 aa from aF, and the first 10aa of EGF. A synthetic linker was prepared which encoded EGF aa11-14 (substituting Glu for Asp$_{11}$), having the following sequence:
GluGlyTyrCysLeuHisAspGlyValCysMetTyrIleGlu
AGGCTACTGTTTGCACGACGGTGTTT-
GTATGTACATCGA
GCTTCCGATGACAAACGTGCTG-
CCACAAACATACATGTAGCTTCGA The linker and the 547 bp fragment were ligated into pBR322 digested with BamHI and HindIII to provide plasmid pBR322/D11E. This vector was digested with BamHI and HindIII to provide a 587 bp fragment. Plasmid pAB24 was linearized with BamHI, and the pAB24 and 587 bp fragments were ligated with the 1026 bp fragment from the BamHI and partial HindIII digest of pGAP/EGF. Plasmid pAB24 contains the complete yeast 2 micron sequence and the complete pBR322 sequence, as well as the yeast URA3 gene (derived from plasmid YEp24, ATCC No. 37051, described by D. Botstein et al, *Gene* (1979) 8:17), and the yeast LEU2$^d$ gene (derived from plasmid pCl/1, described above). Insertion in the BamHI site interrupts the pBR322 ampr gene. The resulting vector was designated pAB24/short/D11E.

pAB24/EGF-D11E

A 1069 bp fragment was obtained from pAB24/short/D11E by digestion with BglI and BamHI. The 1069 bp fragment was ligated to a kinased synthetic linker encoding 4aa of aF and the first 10aa of EGF, having the following sequence:
LeuAspLysArgAsnSerAspSerGluCysProLeuSerHis
CTGGATAAAAGAAACTCCGACTC-
CGAATGTCCATTGAGCCACGA
GACCTATTTTCTTTGAGGCTGAGGCT-
TACAGGTAACTCGGT This fragment was then digested with PvuII and BamHI to provide a 1110 bp fragment. Plasmid pGAP/EGF was digested with BamHI and PvuII to provide a 645 bp fragment encoding the short GAP promoter and the standard aF leader sequence. The 1110 bp fragment was ligated with the 645 bp fragment and pAB24 linearized with BamHI. The resulting plasmid, pAB24/EGF-D11E, was transformed into competent HB101 cells, and verified by HindIII restriction pattern, confirmed by BglI digestion. The vector was then transformed into competent JSC-20 yeast cells, and plated on URA- sorbitol. Individual transformants were then streaked on Leu- sorbitol plates.

(B) Proceeding as in part (A) above, the following additional rhEGF derivatives were prepared: rhEGF-Phe$_4$, rhEGF-Ile$_{24}$, rhEGF-Phe$_{22}$, and rhEGF-Phe$_{29}$.

EXAMPLE 2

(Expression of EGF-Glu$_{11}$)

JSC-20 yeast cells transformed with pAB24/EGF-D11E as described in Example 1 were grown in Leu$^-$media (850 mL yeast minimal media, with 100 mL leucine-minus supplements 10× and 40 mL of 2% glucose). The product was purified from the conditioned medium following the procedure disclosed in C. George-Nascimento et al, *Biochem* (1988) 27:797-802. Briefly, after 72-96 hours the media was collected by centrifugation and concentrated by membrane filtration using an Amicon concentrator (membrane YM2). The concentrated medium was applied to a P-10 gel filtration column (Bio-Rad, Richmond, Calif.) and eluted with 0.1 M acetic acid. The EGF-containing fractions were pooled and concentrated, followed by reverse phase-HPLC using a semi-prep C4 column (10 mm×25 cm). The column was equilibrated with 75% A/25% B (A = 5% aqueous acetonitrile with 0.05% trifluoroacetic acid: B = 80% aqueous acetonitrile with 0.05% trifluoroacetic acid), and eluted with a linear gradient from 25% B to 40% B. The product EGF-Glu$_{11}$ was confirmed by amino acid sequencing using automated Edman degradation.

EXAMPLE 3

(Assay of EGF activity)

EGF-Glu$_{11}$ prepared in Example 2 and native sequence EGF-Asp$_{11}$ (Chiron standard A9C13L) were compared for mitogenic activity. The amount of material necessary to achieve a half-maximal stimulation (ED$_{50}$) of $^3$H-T uptake was determined. The ED$_{50}$ was 0.63 ng/mL for EGF-Glu$_{11}$ and 0.57 ng/mL for EGF-Asp$_{11}$: these results were not statistically different.

The assay was conducted substantially following the method described by D. J. Knauer et al, *J Biol Chem* (1984) 259:5623-31.

Human foreskin fibroblasts were obtained and frozen at the thirteenth passage. Thawed cells are trypsinized, pelleted, and resuspended in a medium containing DMEM, 5% FBS, 1 mM sodium pyruvate, 300 ug/mL L-glutamine, 100 U/mL penicillin, and 100 ug/mL streptomycin. The cells are counted using a hemocytomoeter and 0.4% trypan blue. The cell concentration is adjusted to $1 \times 10^5$ cells/mL using the same medium, and dispensed onto microtiter plates (100 uL/well). The plates are incubated for 5 days in a tissue culture incubator.

EGF-Glu$_{11}$ prepared in Example 2 and native sequence EGF-Asp$_{11}$ are dissolved to make 100 ug/mL solutions. These solutions are used to make serial dilutions of 20, 10, 5, 2.5, 1.25, 0.625, 0.3125, 0.15625, 0.078125, 0.0390625, 0.0195, and 0.00975 ng/mL. Ten uL of each dilution is added to a microtiter plate well, and the plates returned to the incubator and incubated at 37° C. for 18 hours. The cells are then pulsed with $^3$H-thymidine ($^3$H-T), by adding 10 uL of $^3$H-T (100 uCi/ mL) to each well, and incubating for 24 hours. The $^3$H-T is then expelled, and the plates rinsed twice with PBS. To fix the cells, the plates are then incubated twice with 5% trichloroacetic acid (TCA) for 15 minutes at room temperature, followed by incubation twice with 100% MeOH. The plates are then air-dried.

The well contents are then solubilized using 0.3 N NaOH (50 uL/well) for 30 minutes, and transferred to scintillation vials. Scintillation fluid (Ready-Solv EP, 4 mL) is then added to each vial, and the vials counted for 1 minute with a 0-1,000 ($^3$H) window in a Beckman LS3801 counter.

EXAMPLE 4

(Demonstration of Extended Half-life)

EGF-Glu$_{11}$ prepared as described in Example 2 was assayed for storage stability using the following procedure:

Solutions of rhEGF and rhEGF-Glu$_{11}$ were prepared in citrate buffer, pH 3, and were maintained at 45° C. Aliquots were drawn on days 0, 1, 7, and 15, and were analyzed by RP-HPLC (as described in Example 2).

FIG. 1 depicts the chromatograms corresponding to rhEGF-Glu$_{11}$ FIG. 1A shows the chromatogram obtained on day 0. The peak at RT 18.72 corresponds to rhEGF-Glu$_{11}$. FIGS. 1B-D show the chromatograms obtained on day 1, day 7 and day 15 respectively. As demonstrated by the chromatograms, there was little degradation of rhEGF-Glu$_{11}$.

FIG. 2 depicts the chromatograms corresponding to rhEGF (native sequence). FIG. 2A shows the chromatogram obtained on day 0, with the peak at RT 18.62 corresponding to rhEGF. FIGS. 2B-D show that under these conditions rhEGF rapidly degraded to rhEGF-isoaspartyl$_{11}$, corresponding to the peak at RT 21-22. By day 15, the degradation products outweighed the original rhEGF. This demonstrated that rhEGF-Glu$_{11}$ displays much greater stability to low pH conditions than native sequence EGF.

EXAMPLE 5

(Pharmaceutical Compositions)

Pharmaceutical compositions for administering EGF-xxx$_{11}$ of the inventions are prepared as follows:

(A) An EGF-Glu$_{11}$ formulation, is prepared as follows:

| | |
|---|---|
| EGF-Glu$_{11}$ | 1-100 μg |
| HSA | 100.0 mg |
| Methylcellulose | 3.0 g |
| Methyl and propyl parabens | 0.2 g |
| Water for injection qs | 100.0 mL |

The methylcellulose and parabens are dissolved in 90 mL of the water to provide a gel, to which is added the EGF-Glu$_{11}$ and HSA suspended in the remaining 10 mL.

(B) A topical formulation is prepared as follows:

| | |
|---|---|
| EGF-Glu$_{11}$ | 10-200 μg/g |
| Silvadene ® ointment | qs |

The components are blended together, sterile filtered, and packaged under sterile conditions.

(C) A gel suitable for ophthalmic use is prepared as follows:

| | |
|---|---|
| EGF-Glu$_{11}$ | 1-500 μg/mL |
| Neodecadron | qs |

The components are blended together, sterile filtered, and packaged under sterile conditions.

(D) A formulation suitable for oral administration is prepared as follows:

| | |
|---|---|
| EGF-Glu$_{11}$ | 0.05-3.5 mg |
| mannitol | 400.0 mg |

EGF-Glu$_{11}$ and mannitol are combined in solution and lyophilized. The resulting powder may be loaded into capsules or reconstituted with PBS for oral administration. This formulation is useful for treatment of gastric ulcers.

(E) A formulation useful as a corneal storage medium is prepared as follows:

| | |
|---|---|
| EGF-Glu$_{11}$ | 1-500 μg |
| K-Sol ™ | 1.0 mL |

K-Sol ™ is a commercial corneal storage medium, available from Aurora Biologicals, Williamsville, N.Y. The EGF-Glu$_{11}$ is mixed with the medium, and used to store corneal tissue at 4° C. until implanted.

What is claimed:

1. Human EGF-Glu$_{11}$.
2. A pharmaceutical composition for treating a condition treatable with EGF, which composition comprises:
   an effective amount of hEGF-Glu$_{11}$; and
   a pharmaceutically acceptable excipient.

* * * * *